(12) United States Patent
Tamura et al.

(10) Patent No.: US 12,121,298 B2
(45) Date of Patent: Oct. 22, 2024

(54) ABNORMALITY DETECTION SYSTEM, LASER TREATMENT DEVICE, AND LASER TREATMENT SYSTEM

(71) Applicant: J. MORITA MFG. CORP., Kyoto (JP)

(72) Inventors: Yoshiteru Tamura, Kyoto (JP); Yoshihide Okagami, Kyoto (JP); Akihito Hongo, Kyoto (JP); Katsumi Hiyoshi, Kyoto (JP); Haruhiko Murakami, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 1092 days.

(21) Appl. No.: 16/943,206

(22) Filed: Jul. 30, 2020

(65) Prior Publication Data
US 2020/0352648 A1 Nov. 12, 2020

Related U.S. Application Data

(63) Continuation of application No. PCT/JP2019/003096, filed on Jan. 30, 2019.

(30) Foreign Application Priority Data

Jan. 30, 2018 (JP) .................................. 2018-013864

(51) Int. Cl.
*A61B 18/20* (2006.01)
*A61B 1/12* (2006.01)
(Continued)

(52) U.S. Cl.
CPC .............. *A61B 18/201* (2013.01); *A61B 1/12* (2013.01); *G02B 23/2476* (2013.01);
(Continued)

(58) Field of Classification Search
None
See application file for complete search history.

(56) References Cited

U.S. PATENT DOCUMENTS 6,175,580 B1 1/2001 Odaka et al.
9,810,836 B2 * 11/2017 Okagami ............. A61B 18/201
(Continued)

FOREIGN PATENT DOCUMENTS

DE 102011117509 A1 5/2012
JP 11-194068 A 7/1999
(Continued)

OTHER PUBLICATIONS

Office Action dated Jul. 13, 2022, from Japanese Patent Office from corresponding application and English translation.
(Continued)

*Primary Examiner* — Deborah L Malamud
(74) *Attorney, Agent, or Firm* — Capitol City TechLaw, PLLC; Samuel P. Burkholder

(57) ABSTRACT

An abnormality detection system for highly precise detection of an abnormality in a laser treatment device includes a laser transmission tube coupled with a laser treatment unit, oscillating laser light, a discharge-side water pressure sensor, and a water pressure detection liquid surface level meter detecting a change in a pressure of cooling water flowing through forward-direction and a backward-direction spaces in the laser transmission tube. The laser transmission tube includes a hollow wavelength path having a lightguide space formed in a longitudinal direction, and an outer case enclosing an outer circumferential surface of the hollow waveguide path and extending in the longitudinal direction. The discharge-side water pressure sensor and the water pressure detection liquid surface level meter detect the change in the pressure of the cooling water flowing through in a forward-direction space and a backward-direction space to detect any abnormality.

17 Claims, 8 Drawing Sheets

(51) Int. Cl.
  *G02B 23/24*  (2006.01)
  *A61B 18/00*  (2006.01)
  *A61B 18/22*  (2006.01)
  *A61B 90/00*  (2016.01)

(52) U.S. Cl.
  CPC ............ *A61B 2018/00011* (2013.01); *A61B 2018/00023* (2013.01); *A61B 2018/00642* (2013.01); *A61B 2018/00863* (2013.01); *A61B 2018/00982* (2013.01); *A61B 18/22* (2013.01); *A61B 2018/2247* (2017.05); *A61B 2090/064* (2016.02)

(56) References Cited

U.S. PATENT DOCUMENTS

| | | |
|---|---|---|
| 2003/0060813 A1 | 3/2003 | Loeb et al. |
| 2008/0208105 A1 | 8/2008 | Zelickson et al. |
| 2008/0319376 A1 | 12/2008 | Wilcox et al. |
| 2012/0289949 A1 | 11/2012 | Okagami et al. |

FOREIGN PATENT DOCUMENTS

| | | | |
|---|---|---|---|
| JP | 2012120826 A | 6/2012 |
| JP | 2012235888 A | 12/2012 |

OTHER PUBLICATIONS

European Patent Office, Extended European Search Report mailed Sep. 20, 2021, in EP Application No. 19747058.6 (8 pages).
International Search Report conducted by Japan Patent Office for PCT/JP2019/003096 mailed Apr. 23, 2019. (Japanese 2 pages, English 1 page).

\* cited by examiner

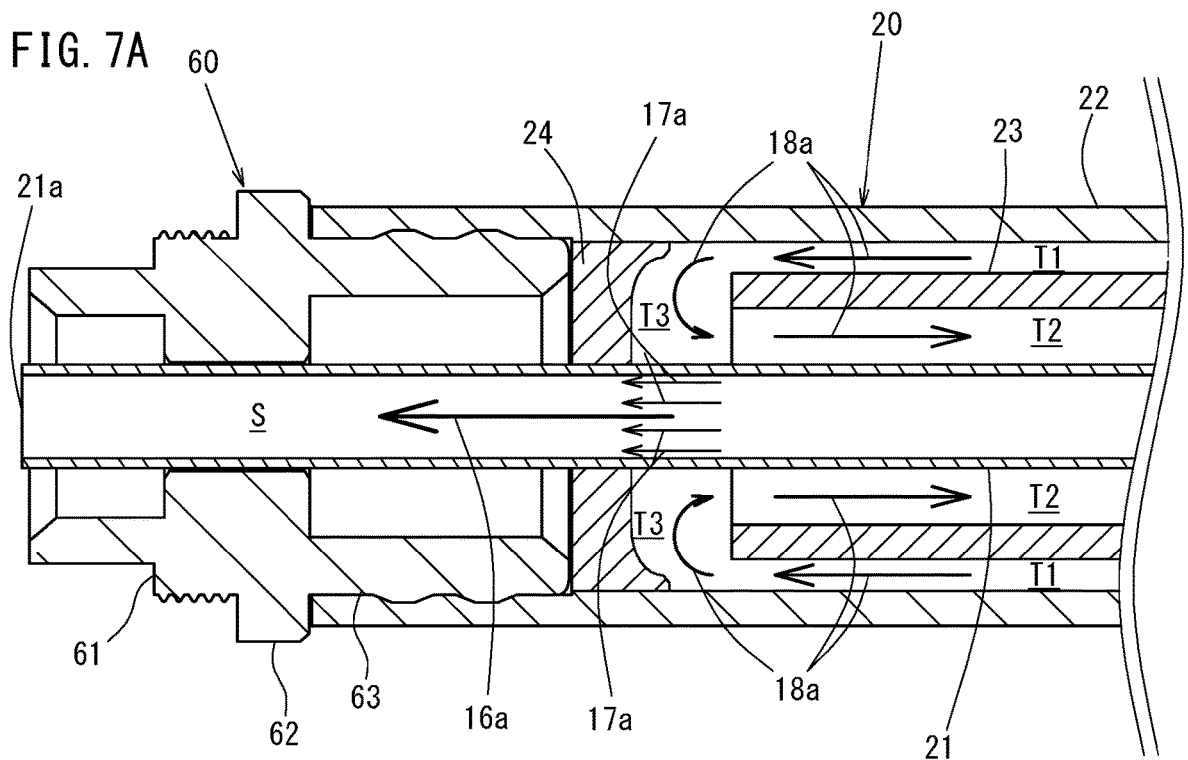
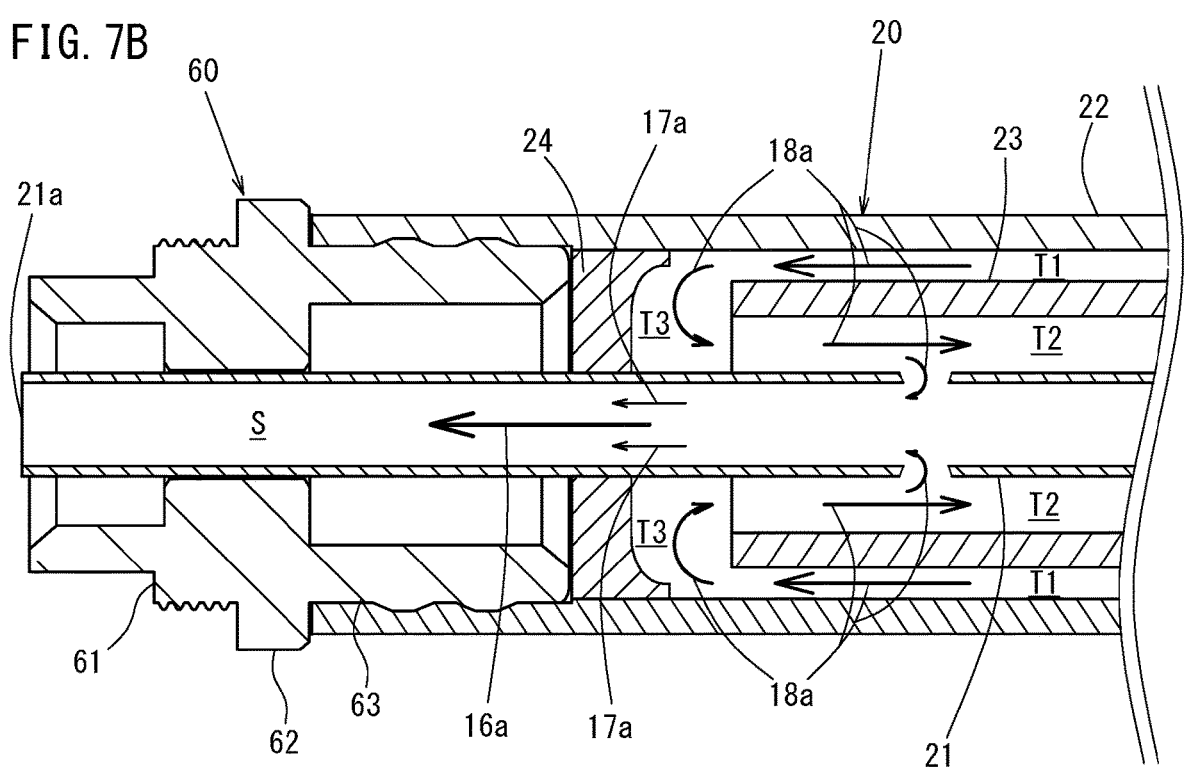

FIG. 8

| | AIR PUMP MALFUNCTION | COOLING WATER PUMP MALFUNCTION | HOLLOW WAVEGUIDE PATH BREAKAGE | PRESSED STATE | NORMAL |
|---|---|---|---|---|---|
| AIR PRESSURE GAUGE 50 | ATMOSPHERIC PRESSURE | — | NORMAL VALUE+10% | NORMAL VALUE+10% | NORMAL VALUE |
| DISCHARGE-SIDE WATER PRESSURE SENSOR 42 | — | — | NORMAL VALUE-10% | NORMAL VALUE | NORMAL VALUE |
| PRESSURE GAUGE 43c | — | — | NORMAL VALUE-10% | NORMAL VALUE | NORMAL VALUE |
| LIQUID SURFACE LEVEL METER 43b | — | — | LOW | HI | HI |
| SUPPLY-SIDE WATER PRESSURE SENSOR 41 | — | NORMAL VALUE-10% | — | NORMAL VALUE | NORMAL VALUE |
| DETECTION TIMING | AFTER START | AT LEAST 40 SECONDS AFTER THE START OF THE COOLING WATER PUMP | AT LEAST 40 SECONDS AFTER THE START OF THE DEVICE | AT LEAST 40 SECONDS AFTER THE START OF THE COOLING WATER PUMP | — |

ABNORMALITY DETECTION SYSTEM, LASER TREATMENT DEVICE, AND LASER TREATMENT SYSTEM

CROSS-REFERENCE TO RELATED APPLICATION

This application is a continuation application of International Application No. PCT/JP2019/003096 filed Jan. 30, 2019, the entire content of which is hereby incorporated by reference in its entity. This application claims priority under 35 U.S.C § 119(a)-(d) to Japanese Patent Application No. 2018-013864 filed Jan. 30, 2018, the entire content of which is hereby incorporated by reference in its entity.

TECHNICAL FIELD

The present invention relates to an abnormality detection system that detects an abnormality of, for example, a laser treatment device, the laser treatment device, and a laser treatment system.

BACKGROUND ART

As a minimally invasive treatment method that imposes little burden on a patient, a treatment method using an endoscope is carried out. According to such a treatment using an endoscope, an endoscope tube is inserted into the body from the oral cavity or the like, and a tip structure portion of the endoscope tube is used to perform a surgical operation.

Appropriate forceps are inserted through a forceps insertion opening called a "channel", and a tip end of the forceps comes out from a forceps outlet of the tip structure portion. The surgical operation is performed by use of the tip end of the forceps. As the forceps, any of various tools including holding forceps, a knife and the like is usable. Especially for an endoscopic submucosal dissection (hereinafter, referred to as "ESD") performed on an early digestive tract cancer, this surgical operation is a target of attention as an effective treatment method imposing little burden on a patient. Recently, there are cases where a laser transmission tube included in a laser treatment device is used together with the endoscope for this surgical operation.

The laser transmission tube, which is to be inserted into the forceps insertion opening includes, for example, a lightguide tube that guides laser light from a base end toward a tip end thereof. The laser light guided through the lightguide tube is directed from the tip end of the laser transmission tube, so that an operation target site such as a cancer or the like may be cauterized, incised, excised or dissected.

Regarding the laser transmission tube, the lightguide tube is curved along with a curing action of the endoscope tube. There is an undesirable possibility that such a curving action breaks the lightguide tube, and the laser light leaks from the broken site to damage a site other than the operation target site. Under the circumstances, some abnormality detection systems that detect such an abnormality of the laser treatment device have been proposed.

For example, the abnormality detection system disclosed in Patent Document 1 includes a first space, which is a hollow space formed in the lightguide tube, and also includes a second space formed outer to the lightguide tube. Laser light and dry gas are provided to flow through the first space. If the lightguide tube is broken in a state where the dry gas flows in this manner, the first space and the second space are communicated with each other. Therefore, the flow rate of the dry gas flowing in the second space is changed. It is described that such a change in the flow rate of the dry gas flowing in the second space is detected, so that the breakage of the lightguide tube may be detected.

However, it is difficult to detect such a change in the flow rate of the dry gas instantaneously and highly precisely. Therefore, with the abnormality detection system disclosed in Patent Document 1, it is difficult to detect the breakage of the lightguide tube in a short time, with certainty and with high precision. In addition, it is difficult to detect an abnormality of a laser treatment device other than the breakage of the lightguide tube and to specify a cause of each of the abnormalities. In such a situation, it is desired to improve the abnormality detection system.

CITATION LIST

Patent Literature

Patent Document 1: Japanese Laid-Open Patent Publication No. Hei 11-194068

SUMMARY OF INVENTION

Technical Problem

In light of the above-described problems, the present invention has an object of providing an abnormality detection system capable of detecting, with high precision, an abnormality of a laser treatment device, for example, a breakage of a lightguide tube, and a laser treatment device and a laser treatment system using the abnormality detection system.

Solution to Problem

The present invention is directed to an abnormality detection system including a laser transmission tube coupled with a laser treatment unit, oscillating laser light, to transmit the laser light; and a cooling portion fluid change detection portion detecting a change in a pressure of a cooling fluid flowing through a cooling space in the laser transmission tube. The laser transmission tube includes a lightguide tube having a lightguide space formed therein, through which the laser light is guided, the lightguide space being formed in a longitudinal direction, and an outer case enclosing an outer circumferential surface of the lightguide tube and extending in the longitudinal direction. The cooling space is formed in the longitudinal direction between the lightguide tube and the outer case. The cooling portion fluid change detection portion detects the change in the pressure of the cooling fluid flowing through the cooling space to detect an abnormality.

The present invention is also directed to a laser treatment device including the above-described abnormality detection system; and the laser treatment unit oscillating the laser light.

The present invention is further directed to a laser treatment system including the above-described laser treatment device; and an endoscope system allowing the laser transmission tube to be inserted therethrough.

The cooling fluid is a fluid that cools the lightguide tube, and encompasses, for example, tap water, ion exchange water, diluted water or another type of liquid; gas such as the air, nitrogen gas, helium gas or the like; powder; and a gel-like substance.

The cooling portion fluid change detection portion may have any structure that detects a change in the pressure of the cooling fluid. For example, the cooling portion fluid change detection portion may have a structure that measures an absolute value of the pressure of the cooling fluid, or a structure that measures a difference between the pressure of the cooling fluid to be provided to the cooling space and the pressure of the cooling fluid to be discharged. Alternatively, in the case where the cooling fluid is a liquid, the cooling portion fluid change detection portion may have a structure including a pressure detection meter that detects a change in a pressure in a liquid storage portion that is sealed between the pressure detection meter and the cooling space and stores the cooling fluid, or may have a structure including a liquid surface level meter that detects a change in the height of the liquid surface level in the liquid storage portion or a change in the amount of the cooling fluid in the liquid storage portion.

The cooling portion fluid change detection portion may include one detection meter or a plurality of detection meters of different functions, for example, a liquid surface level meter and a pressure detection meter.

According to the present invention, an abnormality of the laser treatment device may be detected with high precision.

This will be described in more detail. In the case where, for example, the laser transmission tube is broken or a device supplying the cooling fluid has an abnormality, the pressure of the cooling fluid flowing through the cooling space is changed. This change in the pressure acts on the entirety of the cooling fluid, and therefore, may be detected by the cooling portion fluid change detection portion in a short time and highly precisely. In this manner, the cooling portion fluid change detection portion detects the change in the pressure of the cooling fluid, so that an abnormality of the laser treatment device may be detected with high precision.

In an embodiment of the present invention, gas may flow through the lightguide space, and the abnormality detection system may further include a lightguide portion fluid change detection portion detecting a change in a flow of the gas flowing through the lightguide space.

The gas may be any gas having little influence on the human body, and encompasses nitrogen gas, helium gas or the like as well as the air. Such gas flows through the lightguide tube, through which the laser light is guided. Therefore, it is preferred that the gas does not absorb the laser light.

The change in the flow of the gas flowing through the lightguide space encompasses, for example, a change in the flow rate, a change in the pressure, or a change in the flow speed of the gas flowing through the lightguide space, a change in the temperature, and the like. The lightguide portion fluid change detection portion may include a detection meter that detects one or a plurality of physical quantities.

According to the present invention, it may be specified that the lightguide tube is broken.

This will be described in more detail. In the case where the lightguide tube is broken, a part of the cooling fluid flows into the lightguide space. A part of the cooling fluid that has flown into the lightguide space blocks the flow path of the gas flowing through the lightguide space, and thus the gas flowing through the lightguide space receives a resistance. In addition, a part of the gas flowing through the lightguide space flows into the cooling space. Therefore, the pressure of the cooling fluid is significantly changed. The change in the pressure of the cooling fluid may be detected by the cooling portion fluid change detection portion, and also the change in the flow of the gas may be detected by the lightguide portion fluid change detection portion. In this manner, a combination of the change in the pressure of the cooling fluid and the change in the flow of the gas may cause the breakage of the lightguide tube to be specified.

In the case where, for example, the change in the flow of the gas is not detected by the lightguide portion fluid change detection portion but a change in the pressure of the cooling fluid is detected by the cooling portion fluid change detection portion, it may be specified that the lightguide tube is not broken but the outer case is broken or that there is an abnormality in the device supplying the cooling fluid to the cooling space.

In the case where the change in the pressure of the cooling fluid is not detected by the cooling portion fluid change detection portion but it is detected by the lightguide portion fluid detection portion that the pressure of the gas flowing through the lightguide tube is the atmospheric pressure, it may be specified that the lightguide tube is not broken but there is an abnormality in a device providing the gas to the lightguide tube.

In this manner, the cooling portion fluid change detection portion and also the lightguide portion fluid change detection portion are provided, so that the breakage of the lightguide tube may be detected more accurately, and also an abnormality of the device other than the breakage of the lightguide tube may also be detected.

In an embodiment of the present invention, the lightguide portion fluid change detection portion may detect at least one of a change in a pressure of, and a change in a flow rate of, the gas flowing through the lightguide space.

According to the present invention, for example, the cooling fluid flows into the lightguide space, so that the pressure and the flow rate of the gas is clearly influenced by the cooling fluid. At least one of the change in the pressure and the change in the flow rate of the gas thus influenced is detected by the lightguide portion fluid change detection portion, so that the breakage of the lightguide tube may be specified.

In an embodiment of the present invention, the cooling space may include a forward-direction space causing the cooling fluid to flow in the longitudinal direction in a forward direction from a base end toward a tip end, a backward-direction space causing the cooling fluid, after the cooling fluid flows through the forward-direction space, to flow in the longitudinal direction in a backward direction from the tip end toward the base end, and a communication space communicating the forward-direction space and the backward-direction space to each other at the tip end. The cooling portion fluid change detection portion may detect the change in the pressure of the cooling fluid in the backward-direction space.

The forward-direction space and the backward-direction space may be structured, for example, such that the lightguide tube, the backward-direction space and the forward-direction space are located in this order from the diametrically inner side of the laser transmission tube, such that the lightguide tube, the forward-direction space and the backward-direction space are located in this order from the diametrically inner side, such that the forward-direction space and the backward-direction space are located alternately in a circumferential direction of the lightguide tube, or such that the cooling space is divided into two, namely, into the forward-direction space and the backward-direction space.

According to the present invention, the cooling fluid flows through the forward-direction space and then flows through the backward-direction space via the communication space.

As can be seen, the cooling fluid, while flowing through the backward-direction space, is away from a pump that pumps the cooling fluid toward the cooling space. Therefore, while the cooling fluid is flowing through the backward-direction space, the pressure of the cooling fluid is not easily influenced by the pressure of the pump, and the change in the pressure of the cooling fluid detected by the cooling portion fluid change detection portion is little influenced by noise. For this reason, the change in the pressure of the cooling fluid may be detected with high precision, and thus the breakage of the lightguide tube may be specified with higher precision.

In an embodiment of the present invention, the forward-direction space may be formed outer to the backward-direction space.

According to the present invention, the lightguide tube, the backward-direction space and the forward-direction space in the laser transmission tube are located in this order from the diametrically inner side. Therefore, while flowing through the backward-direction space, the cooling fluid is directly influenced by the breakage of the lightguide tube, and thus the breakage of the lightguide tube may be detected with higher precision.

The cooling fluid, while flowing through the backward-direction space, is away from the pump. Therefore, the cooling fluid flows stably with little influence of noise on the change in the pressure thereof. Therefore, the change in the pressure caused by the breakage of the lightguide tube may be detected with higher precision.

In an embodiment of the present invention, the cooling portion fluid change detection portion may include a liquid storage portion storing a liquid, a liquid surface level in the liquid storage portion being changed in accordance with the change in the pressure of the cooling fluid while the cooling fluid is flowing through the cooling space, and a liquid surface level detection portion detecting a change in the liquid surface level in the liquid storage portion, or a pressure detection portion detecting a change in a pressure in the liquid storage portion.

The liquid to be stored in the liquid storage portion is not limited to the cooling fluid cooling the lightguide tube. A liquid different from the cooling fluid may be stored in the liquid storage portion. The pressure of the cooling fluid stored in the liquid storage portion may be detected, or the change in the pressure of the cooling fluid may be indirectly detected by a change in the liquid surface level or a change in the pressure of another liquid, the liquid surface level or the pressure of which is changed in accordance with the change in the pressure of the cooling fluid.

According to the present invention, the change in the pressure of the cooling fluid flowing through the cooling space acts on the liquid storage portion as the change in the liquid surface level or the change in the pressure of the liquid storage portion. Therefore, such a detection by the liquid surface level detection portion or the pressure detection portion may cause an abnormality of the laser treatment device to be detected with high precision.

In the case where the cooling fluid stored in the liquid storage portion is the liquid, the change in the pressure thereof is detected more easily than in the case where the cooling fluid is gas. Therefore, the change in the pressure of the cooling fluid may be detected more certainly, and thus the breakage of the lightguide tube may be detected with higher precision.

In the case where the lightguide portion fluid change detection portion is provided, when the lightguide tube is broken, the cooling fluid flows into the lightguide tube. Therefore, the flow of the gas flowing through the lightguide tube receives a resistance by the cooling fluid, which is a liquid. As a result, the flow rate and the pressure of the gas is significantly changed. Thus, the breakage of the lightguide tube may be detected certainly by the lightguide portion fluid change detection portion.

In an embodiment of the present invention, the cooling fluid may be water.

According to the present invention, the cooling fluid has no influence on the human body. Therefore, even if the lightguide tube is broken and the cooling water fluid flows into the lightguide tube, there is no influence on the human body. For this reason, the surgical operation may be performed more safely and with no worry about adverse influence. In addition, use of water as the cooling fluid may decrease the cost. The water may be tap water, ion exchange water, diluted water or the like.

Advantageous Effects of Invention

The present invention provides an abnormality detection system capable of detecting, with high precision, an abnormality of a laser treatment device, for example, a breakage of a lightguide tube, and a laser treatment device and a laser treatment system using the abnormality detection system.

BRIEF DESCRIPTION OF DRAWINGS

FIGS. 7A and 7B illustrate a flow of cooling water in the laser transmission tube.

FIG. 8 shows the relationship between causes of abnormalities and detection patterns.

DESCRIPTION OF EMBODIMENTS

Hereinafter, an embodiment of the present invention will be described with reference to the drawings.

Figure 1:
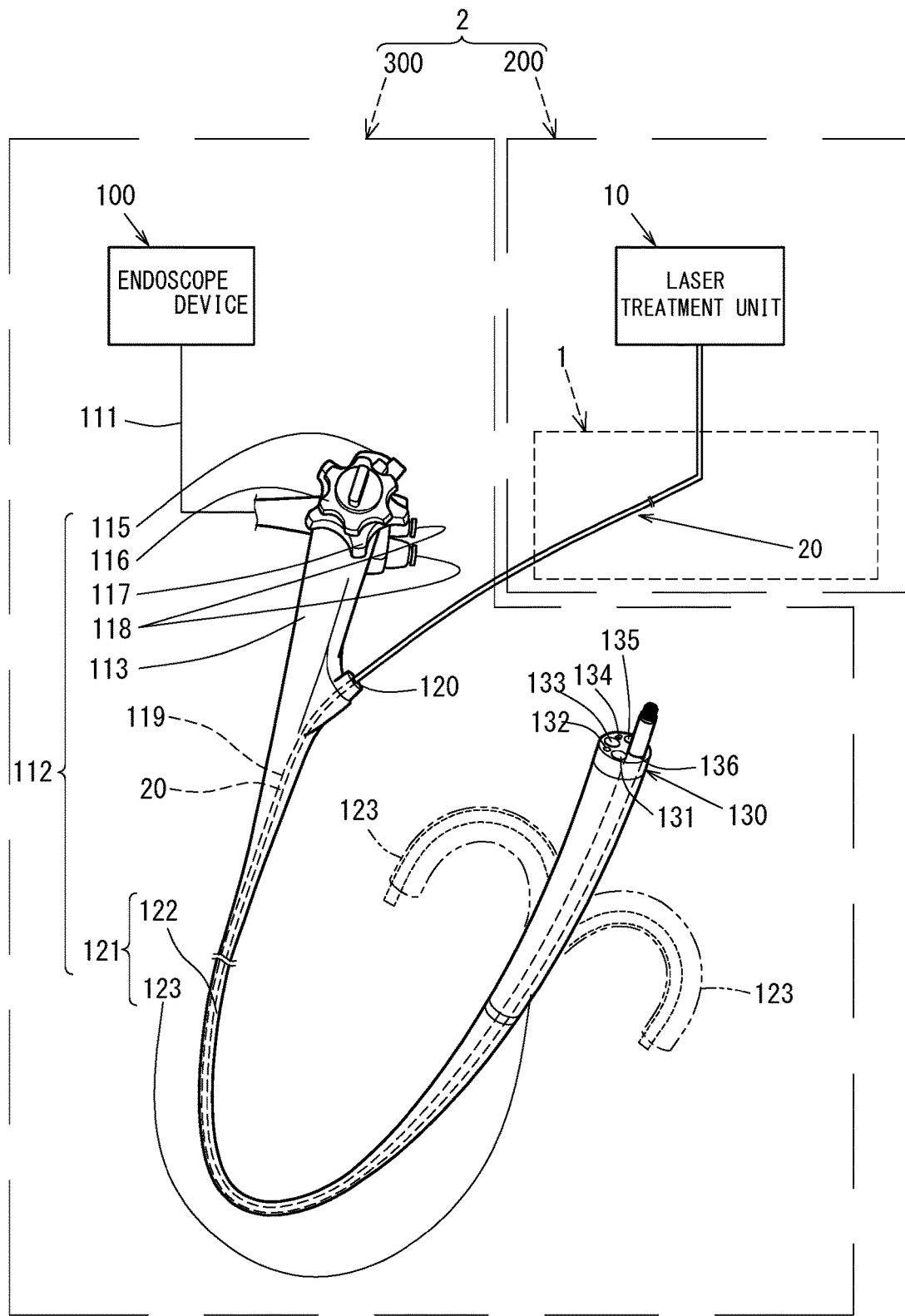
FIG. 1 is a general structural view of a laser treatment system including an endoscope system and a laser treatment device.
Figure 2:
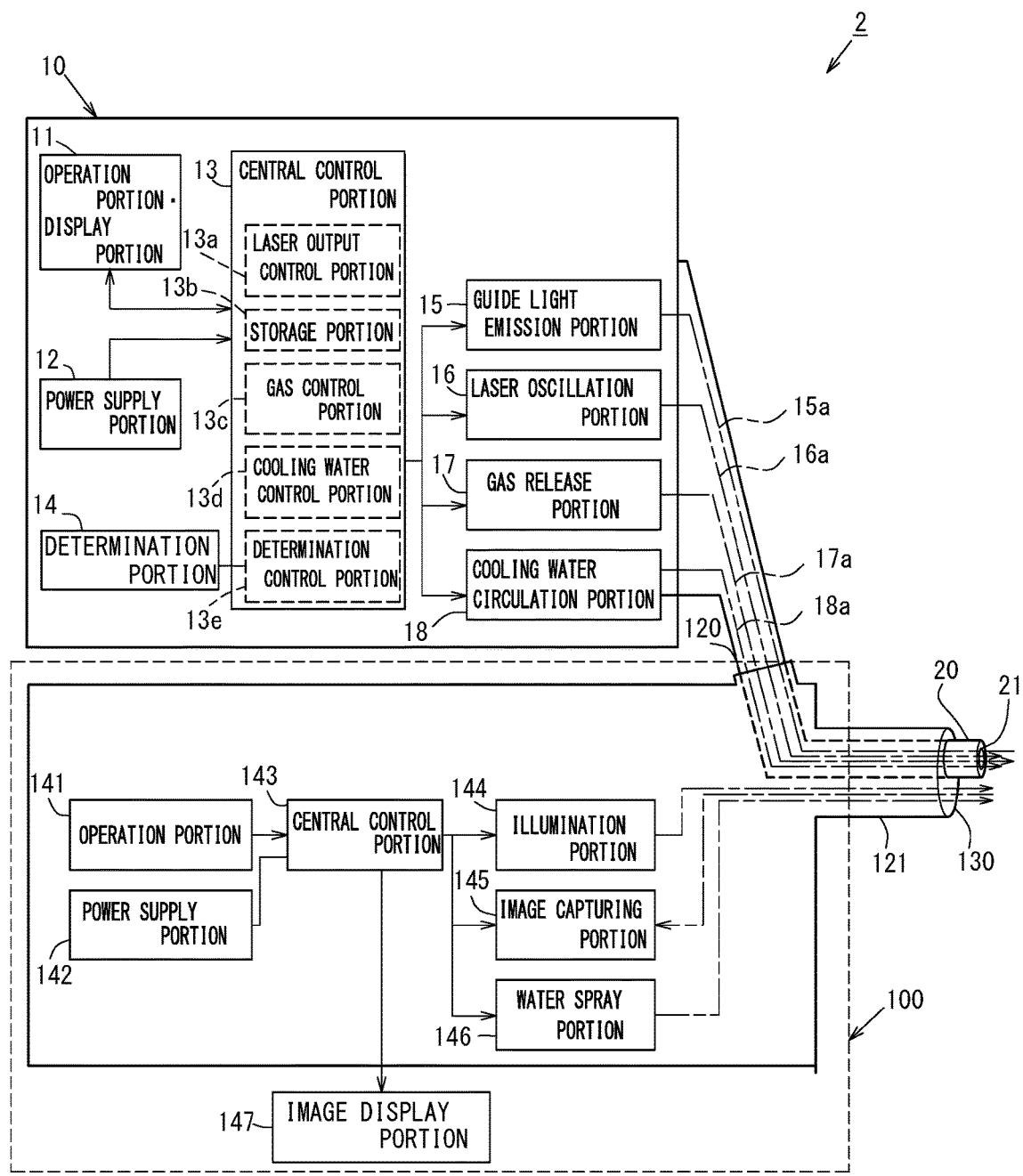
FIG. 2 is a block diagram showing a structure of a laser treatment unit and an endoscope device in the laser treatment system.

FIG. 1 is a general structural view of a laser treatment system 2 including a laser treatment device 200 and an endoscope system 300. FIG. 2 is a block diagram showing a structure of a laser treatment unit 10 and an endoscope device 100 in the laser treatment system 2.

Figure 3:
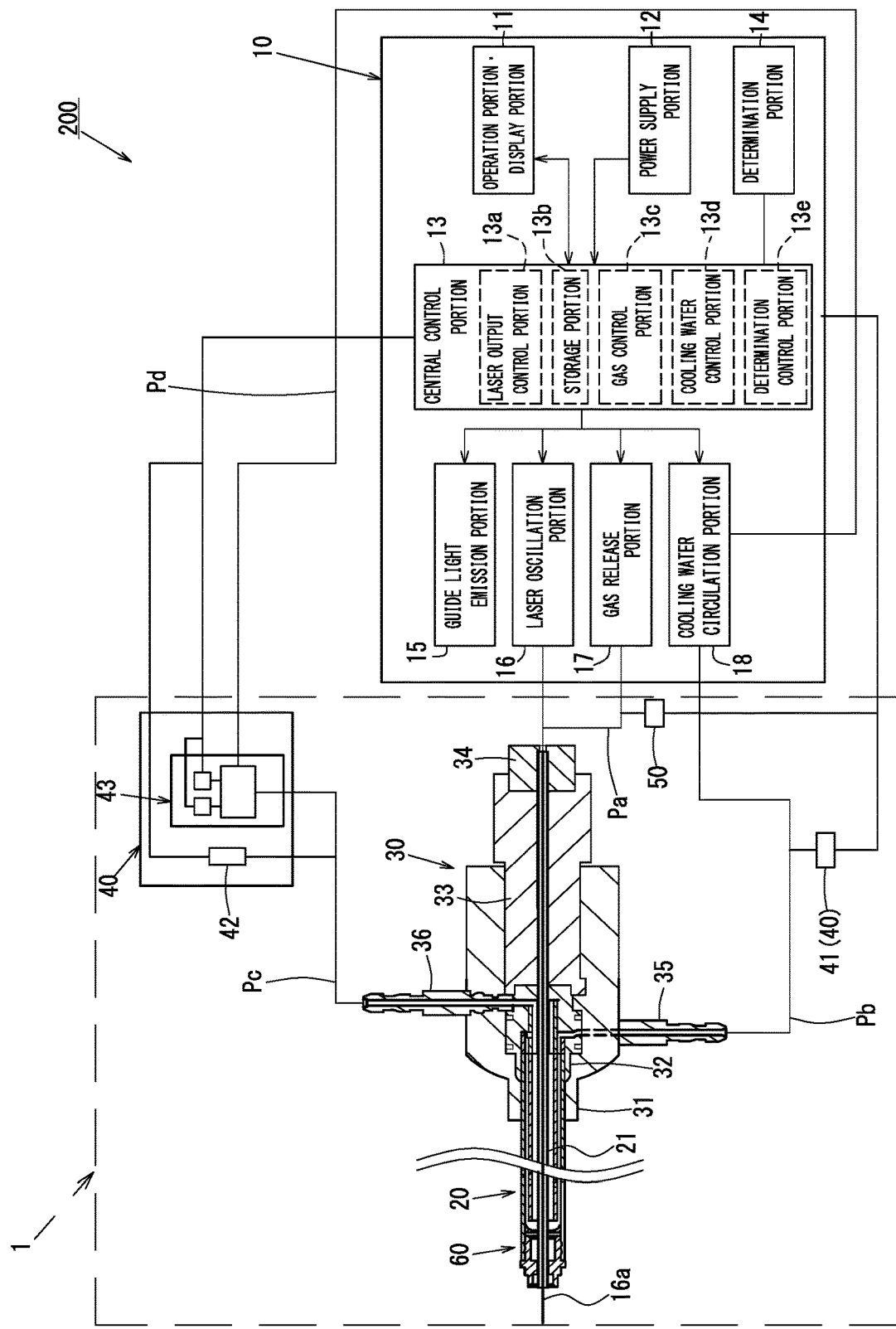
FIG. 3 is a general structural view of the laser treatment device including the laser treatment unit and an abnormality detection system.
Figure 4A:
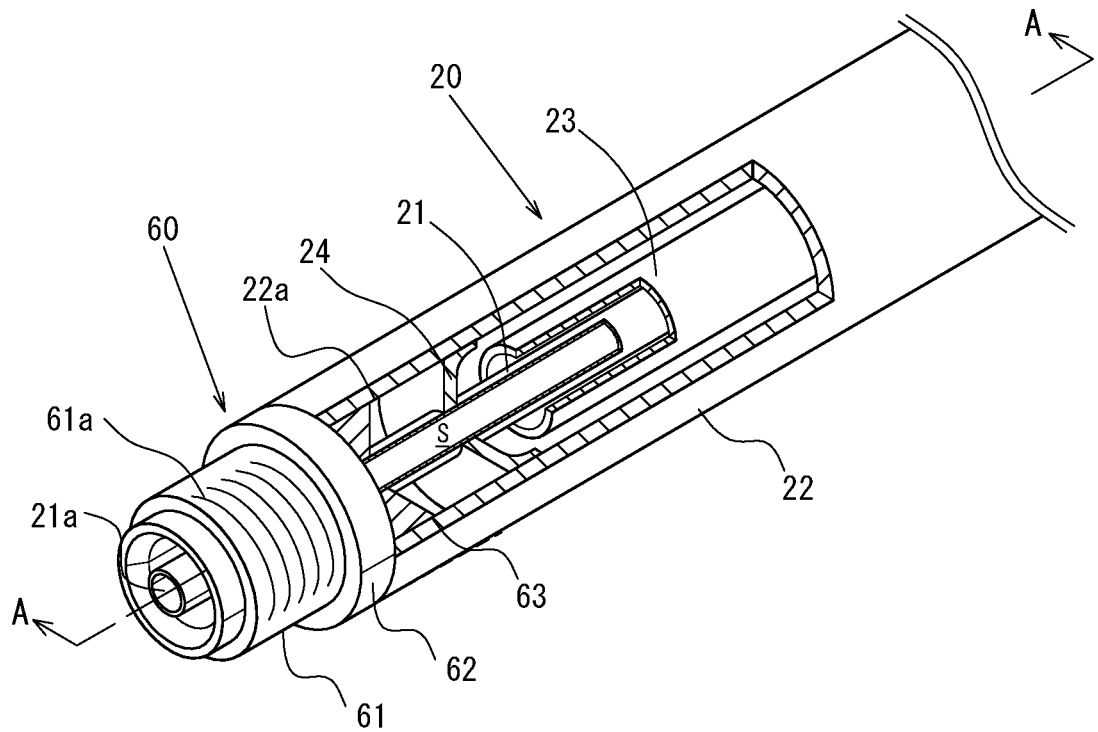
FIGS. 4A and 4B illustrate a laser transmission tube.
Figure 4B:
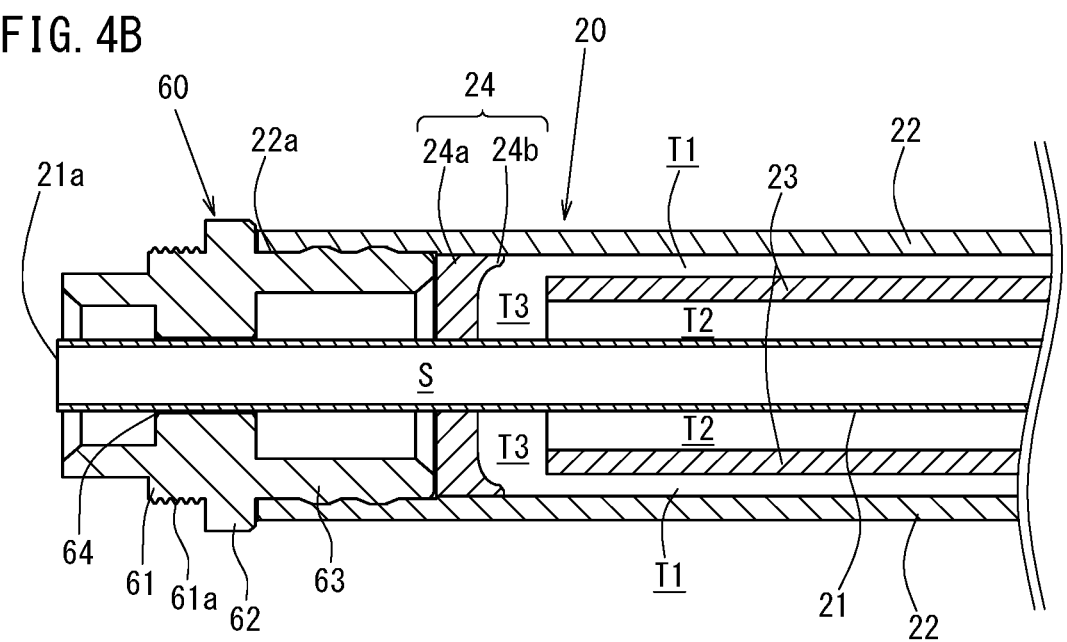
Figure 5:
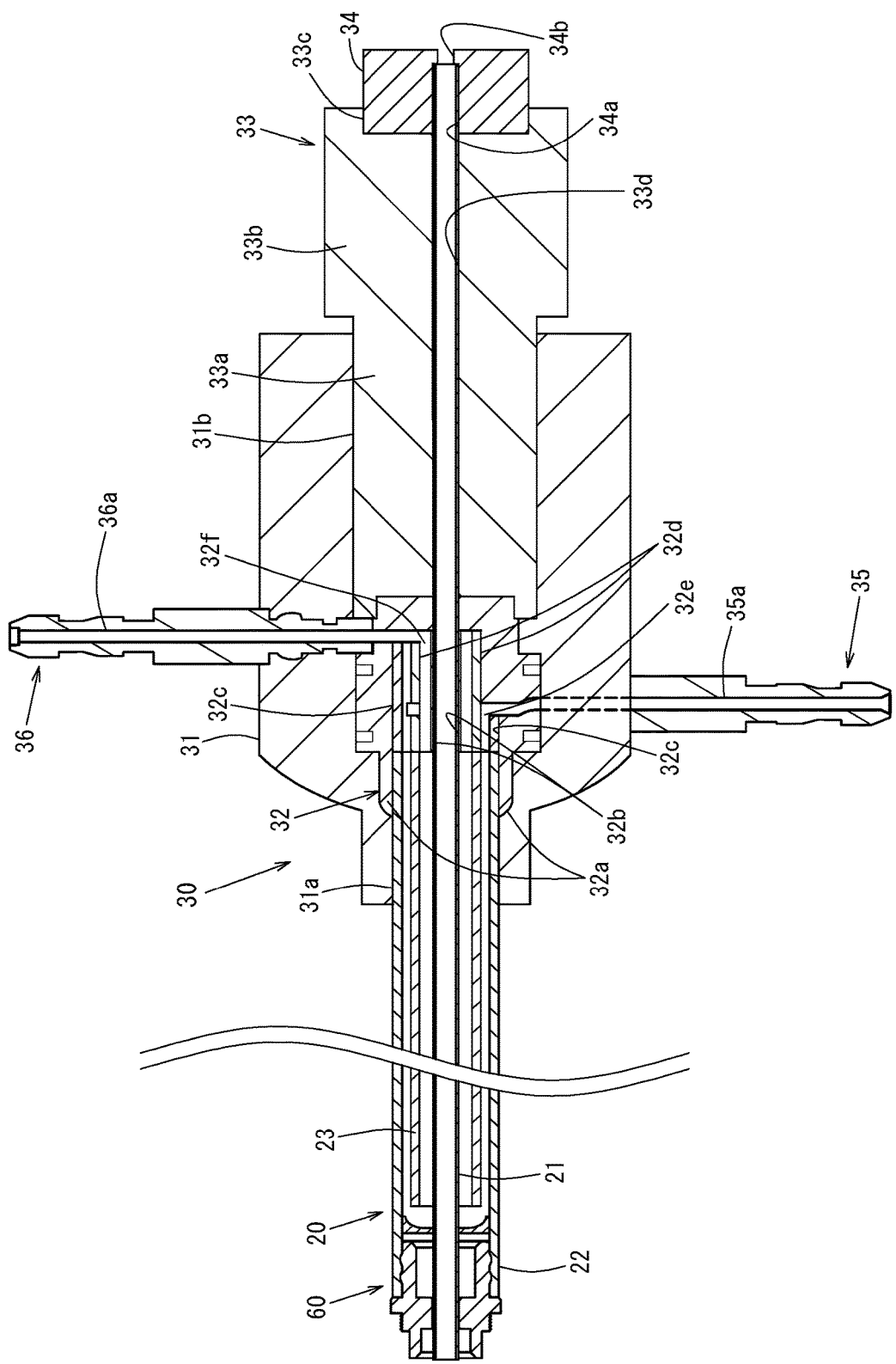
FIG. 5 is a cross-sectional view of the laser transmission tube and a coupling portion.
Figure 6:
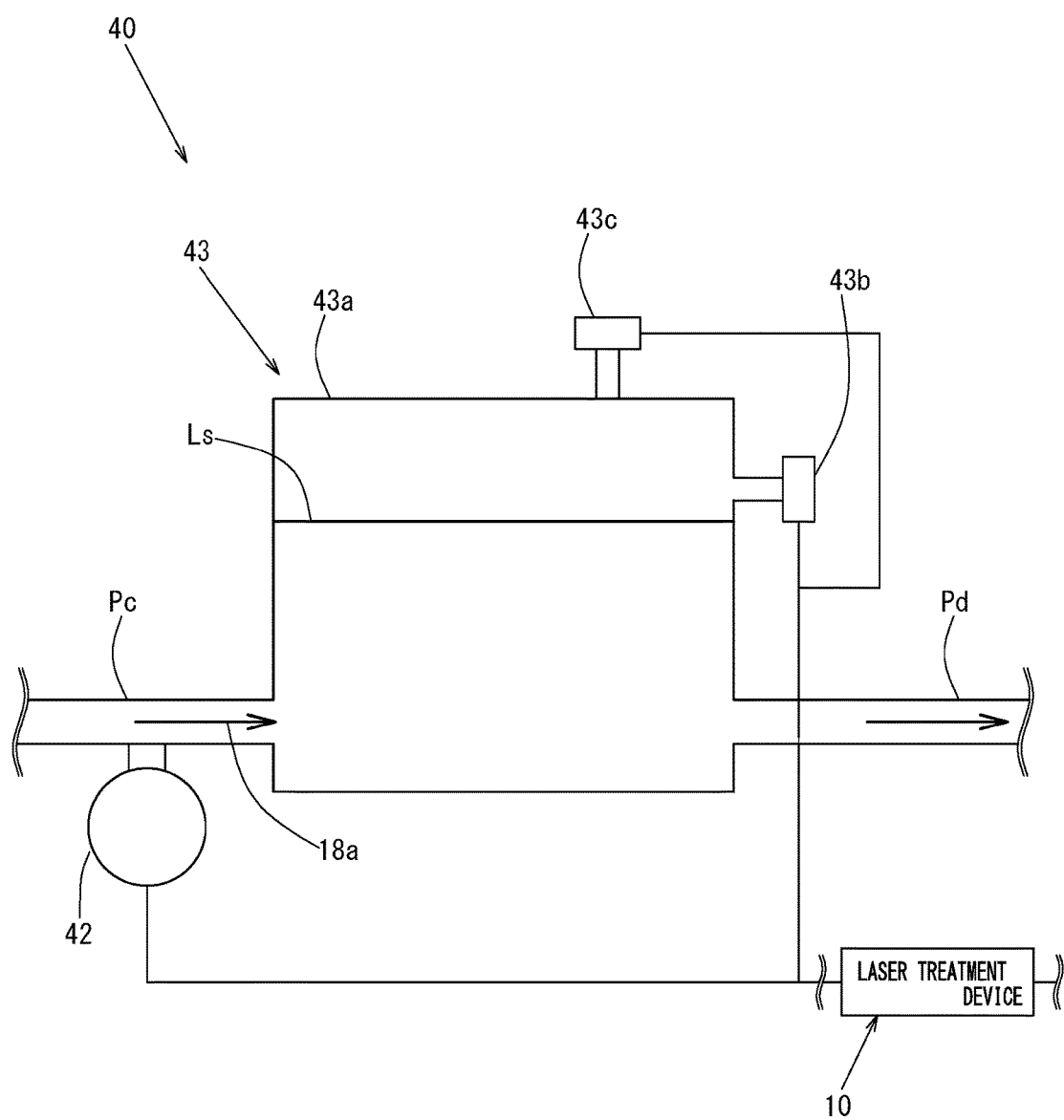
FIG. 6 is a general schematic view of a water pressure detection liquid surface level meter.

FIG. 3 is a structural view showing the laser treatment device 200 including an abnormality detection system 1 and the laser treatment unit 10 in the laser treatment system 2 shown in FIG. 1. The abnormality detection system 1 includes a laser transmission tube 20 and a cooling portion fluid change detection portion 40 (water pressure detection portion 40). FIGS. 4A and 4B illustrate the laser transmission tube 20. FIG. 5 is a cross-sectional view of the laser transmission tube 20 and a coupling portion 30 taken along line A-A in FIG. 4A. FIG. 6 is a general schematic view of a water pressure detection liquid surface level meter 43.

FIGS. 7A and 7B show a flow of cooling water 18a cooling a hollow waveguide path 21. FIG. 8 shows an example of relationship between causes of abnormalities of the devices detected by the abnormality detection system 1 and detection patterns.

FIGS. 4A and 4B and FIGS. 7A and 7B will be described in more detail. FIG. 4A is a general perspective view of a tip portion of the laser transmission tube 20, and FIG. 4B is a cross-sectional view of FIG. 4A taken along line A-A. FIG. 7A is a cross-sectional view of the laser transmission tube 20 taken along line A-A in a state where the hollow waveguide path 21 is not broken, and FIG. 7B is a cross-sectional view of the laser transmission tube 20 taken along line A-A in a state where the hollow waveguide path 21 is broken. FIG. 7A and FIG. 7B show a flow of laser light 16a, the flow of the cooling water 18a and a flow of release gas 17a in the respective states.

FIG. 4A is partially a cross-sectional view in order to clearly show the structure of the laser transmission tube 20.

The laser treatment system 2 to be used with an endoscope for, for example, ESD includes the laser treatment device 200 and the endoscope system 300. The laser treatment device 200 includes the laser treatment unit 10 and the abnormality detection system 1. The abnormality detection system 1 includes the laser transmission tube 20 and the water pressure detection portion 40 coupled with the laser transmission tube 20. The endoscope system 300 includes the endoscope device 100 and an endoscope 112.

Hereinafter, the endoscope device 100 will be briefly described with reference to FIG. 1 and FIG. 2.

As shown in FIG. 1, a main body of the endoscope device 100 is connected with the endoscope 112 via a connection cable 111.

The endoscope 112 mainly includes a scope operation portion 113 and an endoscope tube 121.

The scope operation portion 113 includes an eye contact portion 115, an up-down angle knob 116, a left-right angle knob 117, operation buttons 118, a device insertion opening 120, and the like.

The operation buttons 118 accept operation inputs for air supply, water supply, absorption, zooming and the like.

The endoscope tube 121 includes a flexible tube portion 122, a curved tube portion 123, and a tip structure portion 130 provided in this order from a base portion (rear end) toward a tip end thereof. The endoscope tube 121 has a device insertion path 119 formed therein, which extends from the device insertion opening 120 to a device outlet 136 of the tip structure portion 130. The device insertion path 119 acts as a treatment device insertion path into which a treatment device such as forceps, the laser transmission tube 20 or the like is to be inserted.

In FIG. 1, the endoscope tube 121 is shown as having a diameter increasing from the middle of the flexible tube portion 122 toward a tip end of the curved tube portion 123. This is for easier understanding of the structure of the tip structure portion 130. In actuality, the endoscope tube 121 has a constant diameter suitable to be inserted into a biological organ such as esophagus, stomach, the intestines or the like.

The flexible tube portion 122 has a cylindrical shape that is appropriately curved, and allows an appropriate treatment device, such as forceps or the like, to be inserted from the device insertion opening 120 to the tip structure portion 130. In this embodiment, the laser transmission tube 20 connected with the laser treatment unit 10 via the coupling portion 30 is inserted as the treatment device.

The curved tube portion 123 is operable to be curved in an up-down direction by an operation on the up-down angle knob 116, and is operable to be curved in a left-right direction by an operation on the left-right angle knob 117.

The tip structure portion 130 includes lightguides 131 and 135, a sub water supply inlet 132, a lens 133, a nozzle 134, and the device outlet 136.

The lightguides 131 and 135 are each an illumination portion providing illumination light for image capturing. The lightguides 131 and 135 illuminate the inside of the body, to which light could not have reached otherwise, so that an observation and a surgical operation may be performed.

The sub water supply inlet 132 is a water supply inlet through which a liquid such as washing water, usable to wash an affected area, a stain solution or the like is released in a surgical operation performed with an endoscope.

The lens 133 and an image capturing element located to the rear thereof collect light provided by the illumination performed by the lightguides 131 and 135 and acquire a captured image.

The nozzle 134 is an element that releases, for example, a washing liquid usable to wash the lens 133 toward the lens 133.

The device outlet 136 is an outlet of a treatment device such as, for example, the laser transmission tube 20 connected with the laser treatment unit 10 via the coupling portion 30. The laser transmission tube 20 is formed to be longer than the length of the device insertion path, which is the entire length of the endoscope tube 121.

As shown in FIG. 2, the endoscope device 100 includes an operation portion 141, a power supply portion 142, a central control portion 143, an illumination portion 144, an image capturing portion 145, a water spray portion 146, and an image display portion 147.

The operation portion 141 transmits an operation input provided by the scope operation portion 113 (see FIG. 1) to the central control portion 143. Namely, the operation portion 141 transmits a curving action on the curved tube portion 123 provided by the up-and-down angle knob 116 or the left-right angle knob 117, a pressing action provided by the operation buttons 118, or the like. Separately from the control portion for the endoscope 112, an operation portion is provided in, for example, a controller main body (not shown) of the endoscope device 100, and the operation portion transmits the light amount of the illumination, or an operation of, for example, storing the image capturing of a still image, to the central control portion 143.

The power supply portion 142 supplies operation power to the central control portion 143 and the other portions, and the central control portion 143 executes each of control operations on the respective portions.

The illumination portion 144 executes the illumination with the light provided by the lightguides 131 and 135 (see FIG. 2).

The image capturing portion 145 captures an image transmitted from the lens 133 and the image capturing element (not shown) located to the rear thereof, and acquires a captured image required for the surgical operation or processes the image. Such captured images are acquired successively in real time, so that the operator may perform the surgical operation smoothly.

The water spray portion 146 sprays the liquid from the sub water supply inlet 132. The water spray portion 146 also sprays the liquid from the nozzle 134. The image capturing portion 145 may be provided in the vicinity of the tip structure portion 130 or in the controller main body (not shown) of the endoscope device 100.

The image display portion 147 displays an image in accordance with a signal transmitted from the central control portion 143. This image encompasses the captured image acquired by the image capturing portion 145. Therefore, the operator may perform the surgical operation while checking the captured image displayed on the image display portion 147 in real time.

The laser transmission tube 20 connected with the laser treatment unit 10 included in the laser treatment device 200 is inserted into the device insertion opening 120 of the endoscope 112 connected with the endoscope device 100, thus structured, via the connection cable 111. Thus, the laser treatment system 2 capable of irradiating an operation target site with the laser light 16a may be provided. The endoscope system 300 includes the endoscope device 100 and the endoscope 112.

As shown in FIG. 3, the laser treatment device 200 includes the laser treatment unit 10 and the abnormality detection system 1.

The abnormality detection system 1 will be described in detail with reference to FIG. 3. The abnormality detection system 1 includes the laser transmission tube 20 and the water pressure detection portion 40 coupled to each other via, for example, a supply water tube Pb, a discharge water tube Pc or the like. The water pressure detection portion 40 detects a water pressure of the cooling water 18a flowing in the laser transmission tube 20. An air pressure gauge 50 detecting a change in the release gas 17a to be released to the laser transmission tube 20 is coupled with an air supply tube Pa.

As shown in FIG. 3, the water pressure detection portion 40 is a pressure sensor that includes a supply-side water pressure sensor 41, a discharge-side water pressure sensor 42 and the water pressure detection liquid surface level meter 43, and detects a pressure in each of the supply water tube Pb and the discharge water tube Pc. These pressure sensors will be described below.

As shown in FIG. 2, the laser treatment unit 10 includes an operation portion/display portion 11, a power supply portion 12, a central control portion 13, a determination portion 14, a guide light emission portion 15, a laser oscillation portion 16, a gas release portion 17, and a cooling water circulation portion 18.

The operation portion/display portion 11 accepts an operation input for setting a laser output, changing an operation mode or the like, and transmits such an input signal to the central control portion 13. The operation portion/display portion 11 receives a display signal on conditions for laser output, an operation state of the device or the like from the central control portion 13, and displays appropriate information.

The power supply portion 12 supplies operation power to the central control portion 13 and the other portions.

The central control portion 13 executes each of control operations on the respective portions. The central control portion 13 includes a laser output control portion 13a, a storage portion 13b, a gas control portion 13c, a cooling water control portion 13d, and a determination control portion 13e.

The laser output control portion 13a controls the output and the operation mode set by the operation portion/display portion 11, and also controls the output value of the laser light 16a to be output by the laser oscillation portion 16 in accordance with the determination result of the determination portion 14. The storage portion 13b stores control data such as the output settings, the settings of the operation mode, a reference value for the determination by the determination portion 14, the settings of the operation based on the determination result, and the like, and also stores other appropriate data.

The gas control portion 13c controls the output value of the release gas 17a to be released by the gas release portion 17 in accordance with the output or the operation mode set by the operation portion/display portion 11. The cooling water control portion 13d controls the output value of the cooling water 18a to be output by the cooling water circulation portion 18 in accordance with the output or the operation mode set by the operation portion/display portion 11.

The determination control portion 13e controls the determination portion 14, which determines whether each of measured values is a normal value or an abnormal value based on the numerical values provided by the water pressure detection portion 40 and the air pressure gauge 50 described below and also based on a determination reference value stored on the storage portion 13b. The laser output control portion 13a or the like may control the laser oscillation portion 16, the gas release portion 17, the cooling water circulation portion 18 or the like based on the determination result of the determination portion 14 to execute or stop the illumination with the laser light 16a.

The guide light emission portion 15 emits guide light 15a indicating the position illuminated with the laser light 16a, which is for treatment. With the guide light 15a, the position illuminated with the laser light 16a for treatment may be confirmed.

The laser oscillation portion 16 is controlled by the laser output control portion 13a to execute the oscillation of the laser light 16a for treatment, which is to be used for the surgical operation. In this embodiment, carbon dioxide laser light is used as the laser light 16a. The operations such as settings on the irradiation intensity of the carbon dioxide laser light and start/stop of the illumination with the carbon dioxide laser light are performed by a manual operation on the operation portion/display portion 11 and the control output by the central control portion 13. The manual operation may be partially or entirely replaced with a stepping operation on a foot controller (not shown) provided to be communicable with, and to be capable of controlling, the laser treatment unit 10.

The guide light 15a provided by the guide light emission portion 15 and the laser light 16a oscillated by the laser oscillation portion 16 are all transmitted by one laser transmission tube 20 (see FIG. 2).

The gas release portion 17 includes an air pump (not shown) to be controlled by the gas control portion 13c, and releases the release gas 17 to be provided to the hollow waveguide path 21. The release gas 17 is the air, and is sent toward a base portion of the laser transmission tube 20 via the air supply tube Pa connected with the gas release portion 17 and thus prevents foreign objects from entering the hollow waveguide path 21 (see FIG. 3).

The cooling water circulation portion 18 includes a cooling water pump (not shown) to be controlled by the cooling water control portion 13d. The cooling water circulation portion 18 supplies the cooling water 18a usable to cool the hollow waveguide path 21, which generates heat by the loss of the laser light 16a, and also recovers the supplied cooling water 18a.

The cooling water 18a is transmitted to the laser transmission tube 20 via the supply water tube Pb connected with the cooling water circulation portion 18 including the cooling water pump (not shown), which is to be controlled by the cooling water control portion 13d. After cooling the hollow waveguide path 21, the cooling water 18a is recovered to the cooling water circulation portion 18 via the discharge water tube Pc and a discharge water tube Pd. After being recovered, the cooling water 18a may be circulated and supplied again.

In this embodiment, tap water is used as the cooling water 18a. The amount of the cooling water 18a to be released is controlled by a manual operation on the operation portion/display portion 11 and the control output by the central control portion 13.

The tap water as the cooling water 18a may be replaced with ion exchange water, diluted water; gas such as the air, nitrogen gas, helium gas or the like; or a gel-like substance.

The base portion of the laser transmission tube 20 is formed of a flexible cylindrical body connected with the laser treatment unit 10 via the coupling portion 30. As shown in FIGS. 3, 4A, and 4B, the laser transmission tube 20 includes the hollow waveguide path 21 guiding the laser light 16a from abase end toward a tip end thereof, an outer cover 22 protecting the hollow waveguide path 21, a water path formation tube 23 provided between the hollow waveguide path 21 and the outer cover 22 to enclose an outer circumferential surface of the hollow waveguide path 21, and a tip end portion 24 provided at a tip end of the water path formation tube 23. An attachment portion 60 usable to attach a laser chip (not shown) for any of various purposes is attached to a tip end of the outer cover 22.

The hollow waveguide path 21, which corresponds to a lightguide tube, is a lengthy cylindrical tube having the entirety of an inner circumferential surface thereof covered with a dielectric thin film (not shown). The hollow waveguide path 21 has a lightguide space S formed therein, and also has a laser irradiation opening 21a formed at the tip end thereof. Through the laser irradiation opening 21a, the laser light 16a is to be provided for irradiation.

The cylindrical body forming the hollow waveguide path 21 is formed of a material that has a smooth surface, for example, glass or the like, and that is suitable to form a reflective film of silver or the like and a dielectric thin film. The cylindrical body is formed to be flexible and lengthy. The dielectric thin film is formed of a material appropriate to reflect and transmit the laser light 16a efficiently, for example, COP (cyclic olefin polymer), polyimide or the like.

In this embodiment, the inner circumferential surface of the hollow waveguide path 21 is covered with a silver reflective film and a dielectric thin film. Therefore, the laser light 16a may be guided through the hollow waveguide path 21 (lightguide space S) at high transmission efficiency.

The outer cover 22 is a hollow and flexible annular resin tube. The outer cover 22 has an inner diameter longer than an outer diameter of the hollow waveguide path 21. The outer case 22 has a tip insertion portion 22a formed at the tip end thereof. Through the tip insertion portion 22a, the tip end portion 24 described below is to be inserted.

The water path formation tube 23 is a flexible annular resin tube having an inner diameter longer by a certain degree than the outer diameter of the hollow waveguide path 21 and having an outer diameter shorter by a certain degree than the inner diameter of the outer case 22. The water path formation tube 23 is formed to be shorter than the outer case 22 in a longitudinal direction.

As shown in FIG. 4B, the water path formation tube 23 having such a structure is located between the hollow waveguide path 21 between the outer case 22, which are located away from each other by a certain distance in a diametrical direction. With such an arrangement, a forward-direction space T1 is formed on the diametrically outer side, and a backward-direction space T2 is formed on the diametrically inner side.

As shown in FIG. 4B, the tip end portion 24 is a generally cylindrical body pressed, with pressure, into an inner diametrical portion of the tip insertion portion 22a provided at the tip end of the outer case 22. A tip portion (on the patient side) of the tip end portion 24 in the longitudinal direction is a front-side cylindrical portion 24a, and a rear portion of the tip end portion 24 in the longitudinal direction is a rear-side cylindrical portion 24b. The hollow waveguide path 21 is inserted with pressure into, and held in, a through-hole of the tip end portion 24. Such an arrangement keeps sealability such that water flowing through a communication space T3 communicating the forward-direction space T1 and the backward-direction T2, which are cooling water paths, to each other does not leak from the cooling space (the forward-direction space T1 and the backward-direction T2).

The front-side cylindrical portion 24a is a cylindrical body having a through-hole at a center as seen in a front view. The through-hole has a diameter that is equal to the outer diameter of the hollow waveguide path 21, and extends in the longitudinal direction.

The rear-side cylindrical portion 24b is a cylindrical body extending rearward from an outer peripheral edge of the front-side cylindrical portion 24a. An inner diameter of the rear-side cylindrical portion 24b smoothly expands rearward. In other words, a coupling portion between a rear end of the front-side cylindrical portion 24a and a tip end of the rear-side cylindrical portion 24b is formed to be arced as seen in a cross-sectional view (see FIG. 4B).

The rear-side cylindrical portion 24b having such a structure forms the communication space T3 communicating the forward-direction space T1 and the backward-direction space T2 to each other. The forward-direction space T1 is formed by an inner circumferential surface of the outer case 22 and an outer circumferential surface of the water path formation tube 23. The backward-direction space T2 is formed by the outer circumferential surface of the hollow waveguide path 21 and an inner circumferential surface of the water path formation tube 23.

The attachment portion 60 secured to the outer case 22 by being inserted with pressure into the tip end of the outer case 22 is an attachment tool usable to attach any of various laser chips (not shown) to a tip end of the laser transmission tube 20. The attachment portion 60 includes a laser chip attachment portion 61, a tube coupling portion 62 and an outer case securing portion 63 located in this order from a tip end toward a rear end thereof.

The laser chip attachment portion 61 is a generally cylindrical body having a through-hole, to a tip end of which the laser transmission tube 20 may be secured. The laser chip attachment portion 61 includes a combination of a cylindrical body having an outer diameter shorter than the inner diameter of the outer case 22 and a cylindrical body having an outer diameter slightly longer than the inner diameter of the outer case 22. The laser chip attachment portion 61 has a through-hole formed at a center as seen in a front view. The through-hole has an inner diameter that is equal to the outer diameter of the hollow waveguide path 21.

The laser chip attachment portion 61 includes a thread 61a at an outer circumferential surface thereof. A laser chip (not shown) has a groove formed at an inner wall of an end portion thereof, and the thread 61*a* and the groove are screwed together, so that the laser chip is secured to the thread 61*a*.

The tube coupling portion 62 is a cylindrical body having a minimum inner diameter that is equal to the outer diameter of the hollow waveguide path 21 and an outer diameter longer than an outer diameter of the laser chip attachment portion 61.

As shown in FIG. 4A and FIG. 4B, the outer case securing portion 63 is a cylindrical body having an outer diameter that is generally equal to the outer diameter of the laser chip attachment portion 61. An outer circumferential surface of the outer case securing portion 63 is formed to be mildly rugged, and therefore, the outer case securing portion 63 may secure the attachment portion 60 to the outer case 22.

The attachment portion 60 having such a structure has a through-hole 64 at a center thereof. The through-hole 64 has a diameter that is generally equal to the outer diameter of the hollow waveguide path 21, and extends in the longitudinal direction. The hollow waveguide path 21 is inserted into the through-hole 64 to be secured.

As shown in FIG. 5, the coupling portion 30 coupling the laser treatment unit 10 and the laser transmission tube 20 to each other in a detachable manner includes an outer case body 31, a transmission tube coupling portion 32 provided in the outer case body 31, a hollow waveguide path insertion portion 33, into which the hollow waveguide path 21 is to be inserted, a securing portion 34 securing the hollow waveguide path 21 to the hollow waveguide path insertion portion 33, a supply connection portion 35 to be connected with the supply water tube Pb, and a discharge connection portion 36 to be connected with the discharge water tube Pc. The coupling portion 30 is detachably connected with the laser treatment unit 10 via a cap nut or the like (not shown).

The outer case body 31 is a protective member formed of a metal material. The outer case body 31 has a tip-side insertion hole 31*a* formed at a tip end thereof, into which the base portion of the laser transmission tube 20 may be inserted, and also has a rear-side insertion hole 31*b*, into which the transmission tube coupling portion 32 and the hollow waveguide path insertion portion 33 may be inserted from a rear end thereof.

The transmission tube coupling portion 32 is a bottomed cylindrical body having a through-hole formed at a center as seen in a front view. Into the through-hole, the hollow waveguide path 21 may be inserted. The transmission tube coupling portion 32 is a coupling portion usable to couple and secure the laser transmission tube 20, inserted from the tip-side insertion hole 31*a*, to the laser treatment unit 10. The transmission tube coupling portion 32 includes a holding portion 32*a* holding an outer circumferential surface of a base portion of the inserted outer case 22, an inner wall 32*b* having an inner diameter that is generally equal to the outer diameter of the hollow waveguide path 21, an outer wall 32*c* coupled with the outer case 22, and a partitioning portion 32*d* coupled with the water path formation tube 23.

The holding portion 32*a* is a generally cylindrical body having an inner diameter that is generally equal to an outer diameter of the outer case 22.

The inner wall 32*b* has a through-hole formed at a center as seen in a front view of the transmission tube coupling portion 32. The through-hole has an inner diameter that is generally equal to the outer diameter of the hollow waveguide path 21.

The outer wall 32*c* is a bottomed cylindrical body closed on at a base end thereof, and has an inner diameter and an outer diameter that are generally equal to those of the outer case 22. The outer wall 32*c* is coupled with the outer case 22 of the laser transmission tube 20 inserted from the tip-side insertion hole 31*a*.

The partitioning portion 32*d* is a bottomed cylindrical body closed at a base end thereof, and has an inner diameter and an outer diameter that are generally equal to those of the water path formation tube 23. The partitioning portion 32*d* is coupled with the water path formation tube 23 of the laser transmission tube 20 inserted from the tip-side insertion hole 31*a*.

The outer wall 32*c* and the partitioning portion 32*d* each having such a structure form a first communication portion 32*e* in communication with the forward-direction space T1. Similarly, the inner wall 32*b* and the outer wall 32*c* form a second communication portion 32*f* in communication with the backward-direction space T2. Needless to say, these cooling water tubes are provided with O-rings or the like providing appropriate sealability.

The hollow waveguide path insertion portion 33 is a cylindrical body including a tip end securing portion 33*a* insertable into the rear-side insertion hole 31*b* and a rear end securing portion 33*b* provided at a rear end of the tip end securing portion 33*a*. The rear-end securing portion 33*b* is a cylindrical body having a diameter longer than that of the tip end securing portion 33*a*, and has a cylindrical recess 33*c* formed at a rear end thereof.

The hollow waveguide path insertion portion 33 having such a structure has a securing through-hole 33*d* formed at a center as seen in a front view. The securing through-hole 33*d* has an inner diameter that is generally equal to the outer diameter of the hollow waveguide path 21, and extends in the longitudinal direction.

The securing portion 34 is a cylindrical body formed to be fit into the recess 33*c* formed at the rear end of the hollow waveguide path insertion portion 33. The securing portion 34 has a tip-side insertion hole 34*a* formed in a tip portion thereof. The tip-side insertion hole 34*a* is an insertion hole having a diameter that is generally equal to the outer diameter of the hollow waveguide path 21 and extending in the longitudinal direction. Into the tip-side insertion hole 34*a*, the hollow waveguide path 21 may be inserted. The securing portion 34 has a rear-side through-hole 34*b* formed in a rear portion thereof. The rear-side through-hole 34*b* is a through-hole having a diameter that is shorter than the outer diameter of the hollow waveguide path 21 and extending in the longitudinal direction.

The securing portion 34 having such a structure is fit into the recess 33*c*. With such an arrangement, the securing portion 34 may prevent the hollow waveguide path 21, inserted into the securing through-hole 33*d* formed in the hollow waveguide path insertion portion 33, from coming off from the rear portion of the securing portion 34, and may secure the hollow waveguide path 21 to the hollow waveguide path insertion portion 33 (coupling portion 30).

The supply connection portion 35 in communication with the forward-direction space T1 is a connection portion to be connected with the supply water tube Pb coupled with the cooling water circulation portion 18. The supply connection portion 35 has a supply water path 35*a* formed therein, which is in communication with the first communication portion 32*e*. With such an arrangement, the supply water tube Pb is connected with the supply connection portion 35, so that the cooling water 18*a* may be supplied to the first communication portion 32*e* via the supply water path 35*a*.

Similarly, the discharge connection portion 36 in communication with the backward-direction space T2 is a connection portion to be connected with the discharge water tube Pc, which discharges the cooling water 18a flowing into the backward-direction space T2. The discharge connection portion 36 has a discharge water path 36a formed therein, which is in communication with the second communication portion 32f. With such an arrangement, the discharge water tube Pc is connected with the discharge connection portion 36, so that the cooling water 18a flowing through the second communication portion 32f may be discharged to the discharge water tube Pc via the discharge water path 36a.

The water pressure detection portion 40, which corresponds to a cooling portion fluid change detection portion, is a pressure sensor that detects a pressure in each of the supply water tube Pb and the discharge water tube Pc. As shown in FIG. 3 and FIG. 6, the water pressure detection portion 40 includes a supply-side water pressure sensor 41 measuring the pressure of the cooling water 18a flowing in the supply water tube Pb, a discharge-side water pressure sensor 42 directly measuring the pressure of the cooling water 18a flowing in the discharge water tube Pc, and a water pressure detection liquid surface level meter 43 indirectly measuring the water pressure of the cooling water 18a.

As shown in FIG. 6, the water pressure detection liquid surface level meter 43 includes a water storage portion 43a storing the cooling water 18a flowing from the discharge water tube Pc, a liquid surface level meter 43b detecting a height of a liquid surface level Ls of the cooling water 18a stored in the water storage portion 43a, and a pressure gauge 43c measuring an air pressure in the water storage portion 43a.

The water storage portion 43a is formed of a housing having a certain volume, and may store the cooling water 18a flowing from the discharge water tube Pc. The cooling water 18a stored in the water storage portion 43a is discharged through the discharge water tube Pd. The water storage portion 43a having such a structure is structured such that the liquid surface level Ls is of a certain value in the case where the pressure of the cooling water 18a cooling the hollow waveguide path 21 is of a certain value. The liquid surface level Ls is measured by the liquid surface level meter 43b.

In the case where the liquid surface level Ls in the water storage portion 43a is of a certain value, the air pressure in the water storage portion 43a is also of a certain value. The air pressure in the water storage portion 43a is measured by the pressure gauge 43c.

The measured values of the water pressure detection portion 40 having such a structure are sent to the central control portion 13 and stored on the storage portion 13b. The determination portion 14 determines whether each of the measured values is a normal value or not.

The discharge-side water pressure sensor 42, the water pressure detection liquid surface level meter 43 and the laser transmission tube 20 described above are included in the abnormality detection system 1 detecting an abnormality of the laser treatment device 200 as described below.

In this embodiment, the discharge-side water pressure sensor 42 and the water pressure detection liquid surface level meter 43 are both provided. It is not necessary that both of the discharge-side water pressure sensor 42 and the water pressure detection liquid surface level meter 43 are provided. It is sufficient that only one of the discharge-side water pressure sensor 42 and the water pressure detection liquid surface level meter 43 is provided. It is not necessary that the liquid surface level meter 43b and the pressure gauge 43c are both provided. It is sufficient that only one of the liquid surface level meter 43b and the pressure gauge 43c is provided.

The air pressure gauge 50 (see FIG. 3), which corresponds to a lightguide portion fluid change detection portion, is a pressure gauge that detects a change in the pressure of the release gas 17a flowing in the air supply tube Pa. The pressure value measured by the air pressure gauge 50 is sent to the central control portion 13 and stored on the storage portion 13b. The determination portion 14 determines whether the pressure value is a normal value or not.

The air pressure gauge 50 may be a flow meter that measures a flow rate of the release gas 17a flowing in the air supply tube Pa.

The abnormality detection system 1 having such a structure may detect a breakage of the hollow waveguide path 21 or an abnormality of the laser treatment unit 10.

Hereinafter, a method for detection will be briefly described with reference to FIGS. 7A and 7B.

As shown in FIG. 7A, the cooling water 18a supplied to the supply water tube Pb from the cooling water circulation portion 18 by use of the cooling water pump flows into the first communication portion 32e via the supply water path 35a, and flows through the forward-direction space T1. Since the forward-direction space T1 is in communication with the backward-direction space T2 via the communication space T3, the cooling water 18a flows into the backward-direction space T2 formed around the outer circumferential surface of the hollow waveguide path 21. After flowing through the backward-direction space T2, the cooling water 18a is discharged into the discharge water tube Pc from the second communication portion 32f via the discharge water path 36a, and flows into the water storage portion 43a to be recovered into the cooling water circulation portion 18.

In the case where the hollow waveguide path 21 is broken, as shown in FIG. 7B, a part of the cooling water 18a flowing in the backward-direction space T2 flows into the lightguide space S. Therefore, the amount of the cooling water 18a discharged into the discharge water tube Pc is decreased, and the pressure thereof is also decreased. For this reason, the liquid surface level Ls of the cooling water 18a stored in the water storage portion 43a is lowered, and the air pressure measured by the pressure gauge 43c is also decreased.

The breakage of the hollow waveguide path 21 causes the cooling water 18a to flow into the lightguide space S. This prevents the release gas 17a, which is flowing through the lightguide space S, from flowing toward a tip end thereof. As a result, the air pressure measured by the air pressure gauge 50 is increased.

As described above, in the case where the hollow waveguide path 21 is broken, the pressure values measured by the discharge-side water pressure sensor 42 and the pressure gauge 43a are decreased, and the liquid surface level Ls in the water storage portion 43a detected by the liquid surface level meter 43b is lowered. In addition, the pressure of the release gas 17a measured by the air pressure gauge 50 is increased.

In this manner, a change in the pressure of the cooling water 18a flowing through the laser transmission tube 20 and a change in the pressure of the release gas 17a are detected by, for example, the water pressure detection portion 40, corresponding to the cooling portion fluid change detection portion, and the air pressure gauge 50, corresponding to the lightguide portion fluid change detection portion. Thus, the breakage of the hollow waveguide path 21 may be detected.

For example, as shown in the table of FIG. 8, measured values measured by the discharge-side water pressure sensor 42, the liquid surface level meter 43b, the pressure gauge 43c and the air pressure gauge 50 are respectively compared with reference values stored on the storage portion 13b by the determination portion 14 under the control by the determination control portion 13e. In the case where the measured value of the air pressure gauge 50 is higher than the normal value by 10% and the liquid surface level Ls measured by the liquid surface level meter 43b is lowered (and the measured value of the pressure gauge 43c is lower than the normal value by 10%), it may be detected that the hollow waveguide path 21 is broken. As a result, the laser light 16a may be stopped from being provided under the control by the laser output control portion 13a.

In the case where the measured value of the air pressure gauge 50 is higher than the normal value by 10%, the liquid surface level Ls measured by the liquid surface level meter 43b is not lowered, and the measured value of the pressure gauge 43c is the normal value, it may be detected by the determination of the determination portion 14 that the hollow waveguide path 21 is not broken. In addition, it may be detected that the laser irradiation opening 21a is in a pressed state of being pressed to something. In this case also, the laser light 16a may be stopped from being provided under the control by the laser output control portion 13a.

In this embodiment, for example, it is assumed that the breakage of the hollow waveguide path 21 may be detected effectively 40 seconds after the laser treatment device 200 is started, namely, while the laser treatment device 200 is being stably operated. In the state where the laser irradiation opening 21a is pressed to something, the breakage of the hollow waveguide path 21 may be detected effectively 40 seconds after the cooling water pump provided in the cooling water circulation portion 18 is started, namely, while the cooling water 18a is being stably supplied.

In the case where the measured value of the air pressure gauge 50 is determined as being the atmospheric pressure, it may be detected that the air pump provided in the gas release portion 17 may malfunction. Similarly, in the case where the water pressure value measured by the supply-side water pressure sensor 41 is lower than the normal value by 10%, it may be detected by the determination of the determination portion 14 that the cooling water pump provided in the cooling water circulation portion 18 may malfunction (see FIG. 8). This may cause the central control portion 13 to execute a control of, for example, sounding an alarm or stopping the laser light 16a from being provided.

The values shown in the table of FIG. 8 are merely examples, and may be changed in an appropriate manner by settings or the like. It may be detected that the gas control portion 13c or the cooling water control portion 13d may malfunction, instead of the malfunction of the air pump or the cooling water pump.

As described above, the abnormality detection system 1 includes the laser transmission tube 20 coupled with the laser treatment unit 10, oscillating the laser light 16a, to transmit the laser light 16a, and the discharge-side water pressure sensor 42 and the water pressure detection liquid surface level meter 43 detecting a change in the pressure of the cooling water 18a flowing through the forward-direction space T1 and the backward-direction space T2 of the laser transmission tube 20. The laser transmission tube 20 includes the hollow waveguide path 21 having the lightguide space S, formed in the longitudinal direction, through which the laser light 16a is guided, and the outer case 22 enclosing the outer circumferential surface of the hollow waveguide path 21 and extending in the longitudinal direction. The forward-direction space T1 and the backward-direction space T2 extending in the longitudinal direction are formed between the hollow waveguide path 21 and the outer case 22. The discharge-side water pressure sensor 42 and the water pressure detection liquid surface level meter 43 detect a change in the pressure of the cooling water 18a flowing through the forward-direction space T1 and the backward-direction space T2. Thus, the abnormality detection system 1 detects an abnormality. In this manner, the abnormality detection system 1 may detect an abnormality of the laser treatment device 200 with high precision.

This will be described in more detail. In the case where, for example, the laser transmission tube 20 is broken or the cooling water pump supplying the cooling water 18a malfunctions, the pressure of the cooling water 18a flowing through the forward-direction space T1 and the backward-direction space T2 is changed. This change in the pressure acts on the entirety of the cooling water 18a, and therefore, may be detected by the discharge-side water pressure sensor 42 and the water pressure detection liquid surface level meter 43 instantaneously and highly precisely. In this manner, the discharge-side water pressure sensor 42 and the water pressure detection liquid surface level meter 43 detect the change in the pressure of the cooling water 18a, so that an abnormality of the laser treatment device 200 may be detected with high precision.

This will be described more specifically. In the case where the hollow waveguide path 21 is broken, the cooling water 18a flows into the lightguide space S. Or, the release gas 17a flowing through the lightguide space S flows into the forward-direction space T1 and the backward-direction space T2. As a result, the pressure of the cooling water 18a flowing through the forward-direction space T1 and the backward-direction space T2 is changed. This change in the pressure acts on the entirety of the cooling water 18a, and therefore, may be detected by the discharge-side water pressure sensor 42 and the water pressure detection liquid surface level meter 43 with high precision. Thus, one among the breakage of the hollow waveguide path 21, the breakage of the outer case 22, and an abnormality of the cooling water pump may be detected.

Even in the case where the position of the breakage of the hollow waveguide path 21 is far from the discharge-side water pressure sensor 42 and the water pressure detection liquid surface level meter 43, the change in the pressure may be detected instantaneously because the change in the pressure acts on the entirety of the cooling water 18a.

As described above, the abnormality detection system 1 including the laser transmission tube 20 and the water pressure detection portion 40. Desirably, the pressure detection portion 40 includes the discharge-side water pressure sensor 42 and the water pressure detection liquid surface level meter 43. The discharge-side water pressure sensor 42 and the water pressure detection liquid surface level meter 43 sense the change in the pressure in the laser transmission tube 20. Thus, the abnormality detection system 1 may sense an abnormality of the laser treatment device 200.

The air pressure gauge 50 detecting a change in the pressure of the release gas 17a flowing through the lightguide space S is provided. Therefore, the breakage of the hollow waveguide path 21 may be specified.

This will be described in more detail. In the case where the hollow waveguide path 21 is broken, the cooling water 18a flows into the lightguide space S, or the release gas 17a flowing through the lightguide space S flows into the forward-direction space T1 and the backward-direction space T2. Therefore, the change in the pressure of the cooling water 18a may be detected at least by the discharge-side water pressure sensor 42 or the water pressure detection liquid surface level meter 43, and also the change in the pressure of the release gas 17a may be detected by the air pressure gauge 50. In this manner, a combination of the change in the pressure of the cooling water 18a and the change in the pressure of the release gas 17a may cause the breakage of the hollow waveguide path 21 to be detected. Thus, the breakage of the hollow waveguide path 21 may be specified.

In the case where, for example, the change in the pressure of the release gas 17a is not detected by the air pressure gauge 50 but a decrease in the pressure of the cooling water 18a is detected by the discharge-side water pressure sensor 42 or the water pressure detection liquid surface level meter 43, it may be specified that the hollow waveguide path 21 is not broken but the outer case 22 is broken or that there is an abnormality on the side of the cooling water pump.

In the case where the change in the pressure of the cooling water 18a is not detected by the discharge-side water pressure sensor 42 or the water pressure detection liquid surface level meter 43 but it is detected by the air pressure gauge 50 that the pressure of the release gas 17a flowing through the hollow waveguide path 21 is the atmospheric pressure, it may be specified that the hollow waveguide path 21 is not broken but there is an abnormality on the side of the air pump causing the release gas 17a to flow into the hollow waveguide path 21 (see FIGS. 7A and 7B).

As described above, the air pressure gauge 50 is provided in addition to the discharge-side water pressure sensor 42 and the water pressure detection liquid surface level meter 43. With such a structure, it may be specified whether the hollow waveguide path 21 is broken or not, and also the position of the abnormality other than the breakage of the laser transmission path 20 may be specified.

In the case where, for example, the hollow waveguide path 21 is broken, the cooling water 18a flows into the lightguide space S. Therefore, the release gas 17a is influenced by the cooling water 18a flowing into the lightguide space S. The pressure of the release gas 17a, which is clearly changed, is detected by the air pressure gauge 50. As a result, the breakage of the hollow waveguide path 21 may be specified certainly.

Provided in addition to the above are the forward-direction space T1 causing the cooling water 18a to flow in the longitudinal direction in a forward direction from the base end toward the tip end, the backward-direction space T2 causing the cooling water 18a, after the cooling water 18a flows through the forward-direction space T1, to flow in the longitudinal direction in a backward direction from the tip end toward the base end, and the communication space T3 communicating the forward-direction space T1 and the backward-direction space T2 to each other at the tip end. With such a structure, the discharge-side water pressure sensor 42 and the water pressure detection liquid surface level meter 43 detect the change in the pressure of the cooling water 18a in the backward-direction space T2. Thus, the change in the pressure of the cooling water 18a may be detected with high precision.

This will be described in more detail. The cooling water 18a flows through the forward-direction space T1 and then flows through the backward-direction space T2 via the communication space T3. Thus, the cooling water 18a, while flowing through the backward-direction space T2, is away from the cooling water pump pumping the cooling water 18a toward the forward-direction space T1. Therefore, while the cooling water 18a is flowing through the backward-direction space T2, the pressure of the cooling water 18a is not easily influenced by the pressure of the cooling water pump, and the change in the pressure of the cooling water 18a detected by the discharge-side water pressure sensor 42 and the water pressure detection liquid surface level meter 43 is little influenced by noise. For this reason, the change in the pressure of the cooling water 18a may be detected with high precision, and thus the breakage of the hollow waveguide path 21 may be detected more certainly.

The forward-direction space T1 is formed outer to the backward-direction space T2; namely, the hollow waveguide path 21, the backward-direction space T2 and the forward-direction space T1 are located in this order from the inner diameter side of the laser transmission tube 20. Therefore, the cooling water 18, while flowing through the backward-direction space T2, is directly influenced by the breakage of the hollow waveguide path 21. As a result, the breakage of the hollow waveguide path 21 may be detected more certainly.

The cooling water 18a, while flowing through the backward-direction space T2, is away from the cooling water pump. Therefore, the cooling water 18a flows stably with little influence of noise on the change in the pressure thereof. Therefore, the change in the pressure caused by the breakage of the hollow waveguide path 21 may be detected with high precision.

Further provided are the water storage portion 43a storing the cooling water 18a, which is a liquid, and having the liquid surface level Ls thereof changed in accordance with the change in the pressure of the cooling water 18a while the cooling water 18a is flowing through the forward-direction space T1 and the backward-direction space T2, the liquid surface level meter 43b detecting a change in the liquid surface level Ls in the water storage portion 43a, and the pressure gauge 43c detecting a change in the pressure in the water storage portion 43a. Therefore, the change in the pressure of the cooling water 18a while the cooling water 18a is flowing through the backward-direction space T2 acts as the change in the liquid surface level Ls in, and as the change in the pressure in, the water storage portion 43a. For this reason, the breakage of the hollow waveguide path 21 may be detected by the change in the water surface level in the water storage portion 43a detected by the liquid surface level meter 43b and by the change in the pressure of the water in the water storage portion 43a detected by the pressure gauge 43c.

The change in the pressure of the cooling water 18a, which is tap water, is detected more easily by the discharge-side water pressure sensor 42 and the water pressure detection liquid surface level meter 43 than a change in the pressure of gas. Therefore, the change in the pressure of the cooling water 18a may be detected more certainly, and thus the breakage of the hollow waveguide path 21 may be detected with higher precision.

When the hollow waveguide path 21 is broken, water flows into the hollow waveguide path 21. Therefore, the flow of the release gas 17a receives a resistance by the cooling water 18a, which is a liquid. As a result, the pressure or the like of the release gas 17a is changed. Such a change in the pressure of the release gas 17a is detected by the air pressure gauge 50. Thus, the breakage of the hollow waveguide path 21 may be detected certainly.

The cooling water 18a is tap water. Therefore, even if the hollow waveguide path 21 is broken, the cooling water 18a flowing through the lightguide space S in the hollow waveguide path 21 is safe with no influence on the human body.

Therefore, the surgical operation may be performed with no worry about adverse influence. In addition, use of water as the cooling water 18a may decrease the cost.

The pressure of the cooling water 18a is detected by the discharge-side water pressure sensor 42 and the water pressure detection liquid surface level meter 43. Therefore, the detection may be performed with higher precision.

This will be described in more detail. The discharge-side water pressure sensor 42 detecting the pressure of the cooling water 18a, and the water pressure detection liquid surface level meter 43 detecting the height of the liquid surface level Ls of the cooling water 18a stored in the water storage portion 43a, detect the change in the pressure of the cooling water 18a in different methods. Therefore, as compared with the case where the change in the pressure is detected by only one of the discharge-side water pressure sensor 42 and the water pressure detection liquid surface level meter 43, the change in the pressure of the cooling water 18a may be detected with higher precision.

The lightguide tube according to the present invention corresponds to the hollow waveguide path 21 in the above-described embodiment; and similarly, the cooling fluid corresponds to the cooling water 18a;
the cooling space corresponds to the forward-direction space T1 and the backward-direction space T2;
the cooling portion fluid change detection portion corresponds to the water pressure detection portion 40; more specifically, the water pressure detection portion 40 includes the supply-side water pressure sensor 41, the discharge-side water pressure sensor 42 and the water pressure detection liquid surface level meter 43;
the gas corresponds to the release gas 17a;
the lightguide portion fluid change detection portion corresponds to the air pressure gauge 50;
the liquid storage portion corresponds to the water storage portion 43a;
the liquid surface level detection portion corresponds to the liquid surface level meter 43b; and
the pressure detection portion corresponds to the pressure gauge 43c.

Nonetheless, the present invention is not limited to having the structure in the above-described embodiment, and may be carried out in many other embodiments.

For example, in this embodiment, the release gas 17a is the air. The gas may be any gas having little influence on the human body. The gas may be helium gas, nitrogen gas or the like instead of the air. The release gas 17a flows through the hollow waveguide path 21, through which the laser light 16a is guided. Therefore, it is preferred that the release gas 17a does not absorb the laser light 16a.

In this embodiment, the cooling water 18a is tap water. Alternatively, the cooling water 18a may be another type of water such as ion exchange water, diluted water or the like, or another type of liquid. Still alternatively, gas such as the air, nitrogen gas, helium gas or the like, or a fluid such as powder or gel, may be used instead of the cooling water 18a.

The discharge-side water pressure sensor 42 and the water pressure detection liquid surface level meter 43 corresponding to the cooling portion fluid change detection portion may have any structure that detects the change in the pressure of the cooling water 18a. For example, the discharge-side water pressure sensor 42 and the water pressure detection liquid surface level meter 43 may have a structure that measures an absolute value of the pressure of the cooling water 18a or a structure that measures a difference between the pressure of the cooling water 18a to be provided to the forward-direction space T1 and the backward-direction space T2 and the pressure of the cooling water 18a to be discharged. Alternatively, a change in the difference between the pressure measured by the supply-side water pressure sensor 41 and the pressure measured by the discharge-side water pressure sensor 42 may be detected to detect the change in the pressure of the cooling water 18a.

The water pressure detection portion 40 includes three components of the supply-side water pressure sensor 41, the discharge-side water pressure sensor 42 and the water pressure detection liquid surface level meter 43. It is sufficient that the water pressure detection portion 40 includes, for example, one of the discharge-side water pressure sensor 42 and the water pressure detection liquid surface level meter 43, or two components having different structures. For example, the water pressure detection portion 40 may include a liquid surface level meter and a pressure gauge, more specifically, the water pressure detection liquid surface level meter 43 and the discharge-side water pressure sensor 42. However, it is not preferred that the water pressure detection portion 40 includes only the supply-side water pressure sensor 41 because the supply-side water pressure sensor 41 is close to the cooling water circulation portion 18, and thus such a structure decreases the detection precision of the change in the pressure.

In this embodiment, the change in the pressure of the release gas 17a is measured by the air pressure gauge 50 while the release gas 17a is flowing through the lightguide space S. The target of measurement is not limited to the change in the pressure, but may be, for example, a change in the flow rate or a change in the flow speed of the release gas 17a, or a change in the temperature. A plurality of detectors corresponding to the lightguide portion fluid change detection portion may be provided.

For example, in this embodiment, the change in the pressure of the release gas 17a is measured by the air pressure gauge 50. Thus, as shown in FIG. 8, in the case where the pressure value measured by the air pressure gauge 50 is higher than the normal value by 10% or greater, it may be determined that there is an abnormality that, for example, the hollow waveguide path 21 is broken or the laser irradiation opening 21a is pressed to something. An equivalent effect is provided in the case where, for example, a flow rate meter that measures a change in the flow rate of the release gas 17a is used instead of the air pressure gauge 50.

In this case, referring to FIG. 8, the "normal value+10%" is changed to the "normal value−10%". Namely, in the case where the flow rate of the release gas 17a is lower than the normal value by 10% or greater, it may be determined that there is an abnormality that, for example, the hollow waveguide path 21 is broken or the laser irradiation opening 21a is pressed to something. The value of "10%" is an example in this embodiment, and may be changed appropriately in accordance with the device.

REFERENCE SIGNS LIST

1 Abnormality detection system
2 Laser treatment system
10 Laser treatment unit
16a Laser light
17a Release gas
18a Cooling water
20 Laser transmission tube
21 Hollow waveguide path
22 Outer case
40 Water pressure detection portion (cooling portion fluid change detection portion)

41 Supply-side water pressure sensor
42 Discharge-side water pressure sensor
43 Water pressure detection liquid surface level meter
43a Water storage portion
43b Liquid surface level meter
43c Pressure gauge
50 Air pressure gauge (lightguide portion fluid change detection portion)
100 Endoscope device
200 Laser treatment device
T1 Forward-direction space (cooling space)
T2 Backward-direction space (cooling space)
T3 Communication space
S Lightguide space

The invention claimed is:

1. An abnormality detection system, comprising:
a laser transmission tube coupled with a laser treatment unit, oscillating laser light, to transmit the laser light, and a gas supply tube; and
a cooling portion fluid change detection portion detecting a change in a pressure of a cooling fluid flowing through a cooling space in the laser transmission tube,
the laser transmission tube including:
a lightguide tube having a lightguide space formed therein, through which the laser light is guided, the lightguide space being formed in a longitudinal direction,
the lightguide tube coupled to the gas supply tube to supply gas which flows through the lightguide space, and
an outer case enclosing an outer circumferential surface of the lightguide tube and extending in the longitudinal direction,
the cooling space being formed in the longitudinal direction between the lightguide tube and the outer case,
the cooling space including:
a forward-direction space causing the cooling fluid to flow in the longitudinal direction in a forward direction from a base end toward a tip end,
a backward-direction space causing the cooling fluid, after the cooling fluid flows through the forward-direction space, to flow in the longitudinal direction in a backward direction from the tip end toward the base end, and
a communication space communicating the forward-direction space and the backward-direction space to each other at the tip end, and
the cooling portion fluid change detection portion detecting the change in the pressure of the cooling fluid flowing in the backward-direction space to detect an abnormality.

2. The abnormality detection system according to claim 1, gas flowing through the lightguide space, and
the abnormality detection system further comprising a lightguide portion fluid change detection portion detecting a change in a flow of the gas flowing through the lightguide space.

3. The abnormality detection system according to claim 2, the lightguide portion fluid change detection portion detecting at least one of a change in a pressure of, and a change in a flow rate of, the gas flowing through the lightguide space.

4. The abnormality detection system according to claim 1, the forward-direction space being formed outer to the backward-direction space.

5. The abnormality detection system according to claim 1, the cooling portion fluid change detection portion including:
a liquid storage portion storing a liquid, a liquid surface level in the liquid storage portion being changed in accordance with the change in the pressure of the cooling fluid while the cooling fluid is flowing through the cooling space, and
a liquid surface level detection portion detecting a change in the liquid surface level in the liquid storage portion, or a pressure detection portion detecting a change in a pressure in the liquid storage portion.

6. The abnormality detection system according to claim 1, the cooling fluid being water.

7. A laser treatment device, comprising:
the abnormality detection system according to claim 1; and
the laser treatment unit oscillating the laser light.

8. A laser treatment system, comprising:
the laser treatment device according to claim 7; and
an endoscope system allowing the laser transmission tube to be inserted therethrough.

9. An abnormality detection system, comprising:
a laser transmission tube coupled with a laser treatment unit, oscillating laser light, to transmit the laser light, and a gas supply tube; and
a cooling portion fluid change detection portion detecting a change in a pressure of a cooling fluid flowing through a cooling space in the laser transmission tube,
the laser transmission tube including:
a lightguide tube having a lightguide space formed therein, through which the laser light is guided, the lightguide space being formed in a longitudinal direction,
the lightguide tube coupled to the gas supply tube to supply gas which flows through the lightguide space, and
an outer case enclosing an outer circumferential surface of the lightguide tube and extending in the longitudinal direction,
the cooling space being formed in the longitudinal direction between the lightguide tube and the outer case,
the cooling space including:
a forward-direction space causing the cooling fluid to flow in the longitudinal direction in a forward direction from a base end toward a tip end,
a backward-direction space causing the cooling fluid, after the cooling fluid flows through the forward-direction space, to flow in the longitudinal direction in a backward direction from the tip end toward the base end, and
a communication space communicating the forward-direction space and the backward-direction space to each other at the tip end, and
the cooling portion fluid change detection portion detecting the change in the pressure of the cooling fluid flowing through the cooling space to detect an abnormality.

10. The abnormality detection system according to claim 9,
gas flowing through the lightguide space, and
the abnormality detection system further comprising a lightguide portion fluid change detection portion detecting a change in a flow of the gas flowing through the lightguide space.

11. The abnormality detection system according to claim 10, the lightguide portion fluid change detection portion detecting at least one of a change in a pressure of, and a change in a flow rate of, the gas flowing through the lightguide space.

12. The abnormality detection system according to claim 9, wherein the cooling portion fluid change detection portion detecting the change in the pressure of the cooling fluid in the backward-direction space.

13. The abnormality detection system according to claim 12, the forward-direction space being formed outer to the backward-direction space.

14. The abnormality detection system according to claim 9, the cooling portion fluid change detection portion including:
- a liquid storage portion storing a liquid, a liquid surface level in the liquid storage portion being changed in accordance with the change in the pressure of the cooling fluid while the cooling fluid is flowing through the cooling space, and
- a liquid surface level detection portion detecting a change in the liquid surface level in the liquid storage portion, or a pressure detection portion detecting a change in a pressure in the liquid storage portion.

15. The abnormality detection system according to claim 9, the cooling fluid being water.

16. A laser treatment device, comprising:
the abnormality detection system according to claim 9; and
the laser treatment unit oscillating the laser light.

17. A laser treatment system, comprising:
the laser treatment device according to claim 16; and
an endoscope system allowing the laser transmission tube to be inserted therethrough.

\* \* \* \* \*